United States Patent [19]

Norman et al.

[11] Patent Number: 5,252,733
[45] Date of Patent: Oct. 12, 1993

[54] VOLATILE CROWN LIGAND BETA-DIKETONATE ALKALINE EARTH METAL COMPLEXES

[75] Inventors: John A. T. Norman, Whitehall; Guido P. Pez, Allentown, both of Pa.

[73] Assignee: Air Products and Chemicals, Inc., Allentown, Pa.

[21] Appl. No.: 534,811

[22] Filed: Jun. 5, 1990

[51] Int. Cl.$^5$ .................. C07D 225/00; C07D 323/00
[52] U.S. Cl. ................................ 540/465; 540/469; 549/352
[58] Field of Search ............... 540/469, 465; 549/352

[56] References Cited

U.S. PATENT DOCUMENTS

| | | | |
|---|---|---|---|
| 3,888,877 | 6/1975 | Lehn | 540/469 |
| 3,966,766 | 6/1976 | Lehn | 540/469 |
| 4,156,683 | 5/1979 | Lehn | 540/465 |
| 4,474,963 | 10/1984 | Gokel | 549/352 |
| 4,501,602 | 2/1985 | Miller et al. | 65/18.2 |
| 4,558,144 | 12/1985 | Fay et al. | 556/40 |
| 4,631,119 | 12/1986 | Gokel et al. | 540/352 |
| 4,718,929 | 1/1988 | Power et al. | 65/3.12 |

OTHER PUBLICATIONS

K. Shinohara et al, "Preparation of Y-Ba-Cu- Superconducting Thin Film by Chemical Vapor Deposition," Japanese Journal of Applied Physics, vol. 27, No. 9, pp. L1683-L1685 (1988).

K. Fujiura et al, "Organometallic Chemical Vapor Deposition of $ZrF_4$-Based Fluoride Glasses," Japanese Journal of Applied Physics, vol. 28, No 1, Jan., 1989, L147-L149.

A. P. Purdy, et al, "Chemical Vapor Deposition Experiments Using New Fluorinated Acetylacetonates of Calcium, Strontium, and Barium", Inorg. Chem., (1989) 28), pp. 2799-2803.

Y. Hisanori, et al, "High Critical-Current Density of Y-Ba-Cu-O Superconducting Prepared Films by CVD," Supercond. Sci. Technology. 2 (1989), pp. 115-117.

A. F. Panson, et al, "Chemical Vapor Deposition of $YBa_2Cu_3O_7$ Using Metalorganic Chelate Precursors," Appl. Phys. Lett. 53 (18) pp. 1756-1758 (1988).

R. E. Sievers, et al, "Volatile Metal Complexes," Science, vol. 201, No. 4352, p. 217, (1978).

J. C. Huffman, et al, "Synthesis of a Monopentamethylcyclopentadienyl Halide Complex of Calcium. The X-Ray Crystal Structure of [$(Me_5C_5)Ca(\mu-I)(THF)_2]_2$," Organometallics, vol. 8, No. 8, 2045 (1989).

TNO Institute, "Suitability of Metal $\beta$-diketonates as MOCVD-Precursors for High Tc Superconductors," (1989).

Primary Examiner—C. Warren Ivy
Assistant Examiner—Raymond Covington
Attorney, Agent, or Firm—Mary E. Bongiorno; James C. Simmons; William F. Marsh

[57] ABSTRACT

Volatile $\beta$-diketonate alkaline earth metal complexes useful in chemical vapor deposition (CVD) operations are formed using a cyclic ligand, such as a macrocyclic crown ether, to increase the degree of coordination and shielding around the individual metal ions in the diketonate structure. The resultant monomeric complexes readily volatize to give a chemically stable vapor.

11 Claims, 4 Drawing Sheets

VOLATILE CROWN LIGAND BETA-DIKETONATE ALKALINE EARTH METAL COMPLEXES

TECHNICAL FIELD OF THE INVENTION

The present invention relates to volatile alkaline earth metal β-diketonate metal complexes.

BACKGROUND OF THE INVENTION

In the Chemical Vapor Deposition (CVD) fabrication of alkaline earth metal (i.e. barium, strontium, etc.) containing materials there is a growing need for cleanly volatile sources of these metals that can deliver steady gas phase mass transport of metal-containing vapor during the CVD process. It is especially important that the metal containing vapor is stable and, therefore, of constant chemical formulation. This permits precise control over the elemental composition of the final product. Examples of alkaline earth metal containing materials produced in the CVD process are high temperature superconducting ceramic thin films and ultra-low loss heavy metal fluoride glasses for use in high transmittance optical fibers. In the former case a vapor containing the "volatile" organometallic compound barium bis(hexafluoroacetylacetonate), i.e. ba(hfac)$_2$, along with volatile compounds of yttrium and copper, is contacted with oxygen gas at 10 torr pressure and 500° C. to deposit a thin film of high temperature superconducting ceramic of the formulation yBa$_2$Cu$_3$O$_x$ onto a sapphire substrate. K. Shinohara et al *Jpn. J. Appl. Phy.*, 27 (9), L1683 (1988). In the latter case a vapor containing the volatile compound barium bis(1,1,1,2,2,3,3-heptafluoro-7,7-dimethyl-4,6-octanedione) along with a volatile zirconium compound is contacted with hydrogen fluoride gas at 10-15 kPa pressure at 210° C. to yield BaF$_2$ and ZrF$_4$ respectively. These fluorides are then further processed into high transmittance optical fibers. K. Fujiura et al *Jpn. J. Appl. Phy.*, 28 (1), L147-149 (1989).

The CVD process of forming metal fluorides from volatile sources is a well established technology for metals that readily form volatile complexes such as Be, Al, Zr; see for example U.S. Pat. No. 4,718,929. However, in general, a major requirement in any CVD processing of alkaline earth metal compounds of barium, calcium, and strontium is the need for cleanly volatile sources of these elements. Even though alkaline earth β-diketonate complexes have been utilized in CVD processes, it is well known that they tend to decompose upon sublimation so their effectiveness as precursors for CVD processes is limited by this problem. A. P. Purdy et al *Inorg. Chem.* (28) 2799-2803 (1989).

One approach towards solving the problem of preparing volatile alkaline earth metal compounds has been to synthesize β-diketonate complexes of these elements wherein the β-diketonate ligands contain bulky groups (i.e. t-butyl or fluorinated groups such as CF$_3$ or -CF$_2$CF$_2$CF$_3$). Alkaline earth complexes such as barium bis(2,2,6,6-tetramethyl-3,5-heptanedionate) or barium bis(1,1,1,2,2,3,3-heptafluoro-7,7-dimethyloctane-4,6,-dione) that bear these structural features have been utilized as volatile sources in CVD processes as taught by Y. Hisanori et al *Supercond. Sci. Technology* 2, 115-117 (1989) and A. J. Panson et al *Appl. Phys. Lett.* 53 (18), 1756-8 (1988). These two strategies of using sterically demanding ligands and fluorocarbon character are well known to increase the volatility of metal β-diketonate complexes. Sievers, R. E., *Science*, 201, 217 (1978). This is thought to occur by effecting a reduction in intermolecular association via the shielding of metal centers from each other. However, in the case of alkaline earth metal complexes, such ligands are limited in their ability to promote volatility since they cannot completely supply the degree of coordination or steric shielding that is demanded by these metals. This lack of complete shielding leads to ligands becoming at least partially coordinated (i.e. shared) between two or more metal centers. This in turn leads to polymeric or highly associated involatile compounds. This effect is well known for other alkaline earth complexes that contain simple ligands (i.e. methyl or ethyl organic groups) which are unable to supply the degree of shielding required to stabilize the complexes against polymerization. Huffman, J., *Organometallics*, vol 8 no. 8 2045 (1989).

The volatilities of metal β-diketonate complexes can be increased by coordinating small neutral molecules to the metal centers of these compounds to form volatile "adducts". This helps to prevent ligands being shared between metal centers and thereby promotes more monomeric and hence more volatile compounds. Examples of such small molecules which have been used to increase the volatility of both magnesium and zinc β-diketonates are tetrahydrofuran (THF) and 1,2-dimethoxyethane (diglyme) as taught in U.S. Pat. Nos. 4,501,602 and 4,558,144. Recently TNO Co. (Division of Technology for Society, Dept. of Chemistry, Zeist, The Netherlands) claim to have prepared volatile derivatives of various alkaline earth β-diketonates by treating parent complexes with various linear polyether glymes such as tetraglyme. However, a problem with the approach of adding simple linear coordinating molecules to alkaline earth β-diketone complexes is that under heating conditions they can dissociate from the metal centers thereby precluding the sublimation of the entire adduct. This also causes the chemical composition of the vapor emitting from the sublimation process to be constantly changing. This translates to a loss of mass transfer control in the CVD process.

BRIEF SUMMARY OF THE INVENTION

The present invention is a class of volatile β-diketonate alkaline earth metal complexes which are prepared by treating an alkaline earth metal hydride with a fluorinated β-diketone ligand in the presence of a cyclic ligand containing from 6 to 8 donor groups. The key aspect of this invention is the use of a cyclic ligand, such as a macrocyclic crown ether type compound, to increase the degree of coordination and shielding around individual metal ions in the alkaline earth β-diketonates. Thus these normally oligomeric and highly associated compounds are transformed into stable monomeric complexes that readily and cleanly volatilize to give a chemically stable vapor.

DETAILED DESCRIPTION OF THE INVENTION

Figure 1:
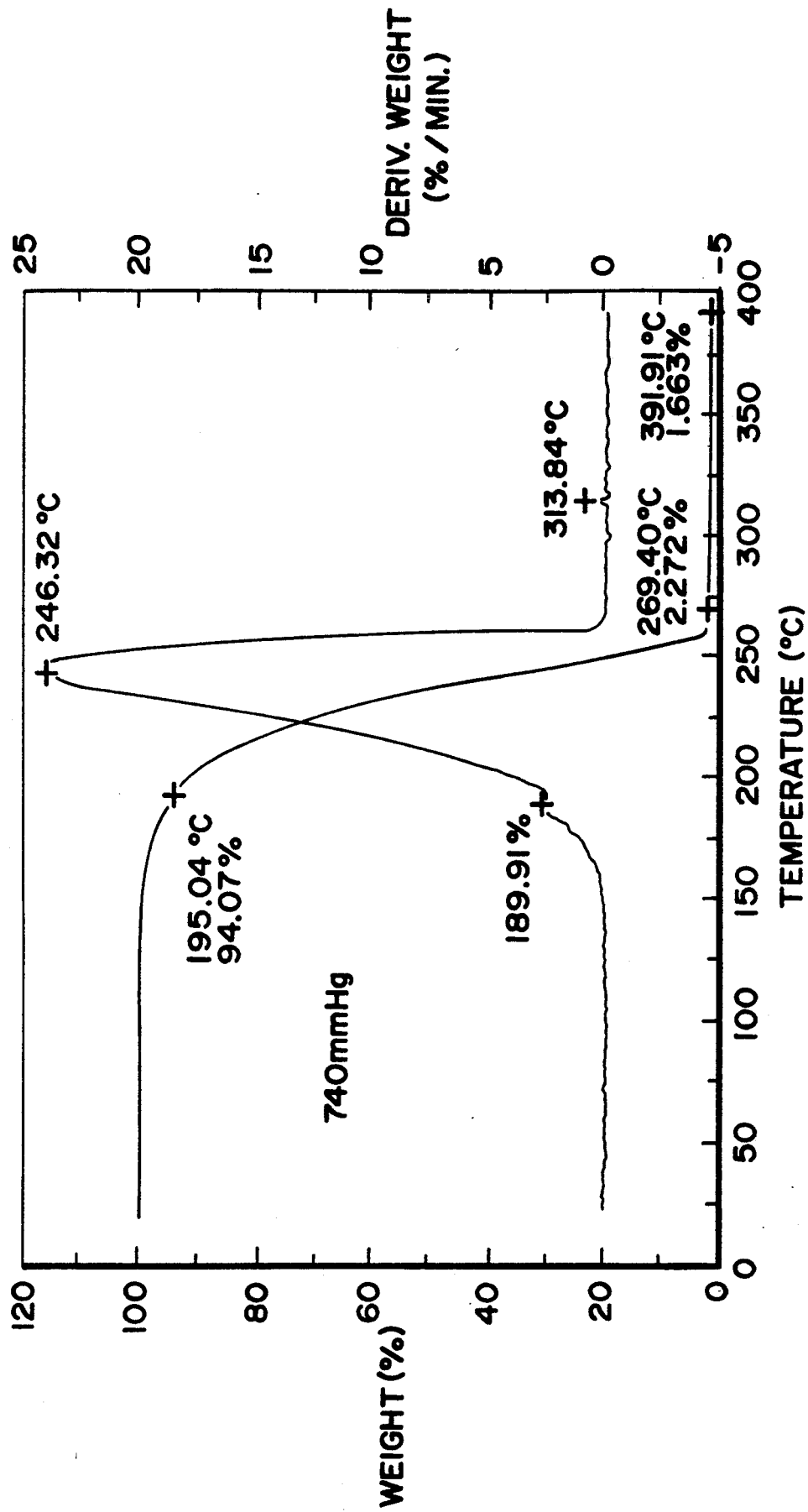
FIG. 1 is a graph of the sublimation characteristics of Ba(hfac)$_2$18-crown-6.

The preparation of thermally stable volatile metal complexes of alkaline earth metals presents a major challenge. For instance, organometallic alkaline earth type complexes are well known to readily form involatile polymers or compounds of marginal thermal stability. For compounds to be volatile, they ideally need to be both monomeric and thermally stable. The propensity of alkaline earth complexes to form polymeric structures stems from their need for large spheres of coordination; i.e., they require a large number of ligands to interact with each metal ion. This is mostly due to the large physical size of the ion. Frequently, this high degree of coordination cannot be completely provided by commonly used ligands such as $\beta$-diketonates.

It has now been found that stable, volatile $\beta$-diketonate alkaline earth metal complexes can be prepared by treating the appropriate alkaline earth metal hydride with a $\beta$-diketone ligand, which is at least partially fluorinated, in the presence of a cyclic ligand containing from 6 to 8 donor groups, such as a macrocyclic "crown ether" type compound. The monomeric nature of barium(hfac)$_2$4,13-diaza-18-crown-6 and barium(hfac)$_2$18-crown-6 in the gas phase has been indicated by Fast Atom Bombardment Mass Spectra which in both cases showed a strong "parent ion", i.e. individual molecules of crown ligand complex. In addition an x-ray crystal structure of the barium(hfac)$_2$18-crown-6 complex was obtained from a single crystal grown by sublimation, also indicating a monomeric; i.e. non-associated, structure.

The resultant volatile, divalent metal $\beta$-diketonate complexes can be represented by the general structural formula:

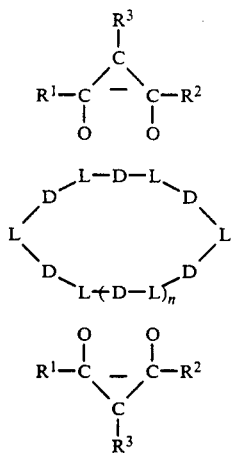

wherein:
- $M^{+2}$ is a divalent metal ion from the alkaline earth series or from the lanthanide series;
- each $R^1$ and $R^2$ are independently a linear or branched $C_1$–$C_4$ perfluoroalkyl group or a fluorophenyl group;
- each $R^3$ is independently H, a halogen, phenyl or a $C_1$–$C_4$ alkyl or fluoroalkyl group;
- each D is independently a donor group selected from

wherein R is H or $C_1$–$C_4$ alkyl;
- L is $(CR_2)_x$ wherein each R is independently H or $C_1$–$C_4$ alkyl and x is an integer from 1 to 4, or L is part of a cyclic aromatic or aliphatic ring; and
- n is an integer from 1 to 3.

In a preferred embodiment, $M^{+2}$ is selected from the group consisting of $Ca^{+2}$, $Sr^{+2}$, $Ba^{+2}$ and $Ra^{+2}$; and most preferably is $Ba^{+2}$. The cyclic ligand formed by D and L must contain from 6 to 8 donor groups (i.e., "D" groups) with ligands wherein all the donor groups are —O— or —NH— or a combination thereof are preferred. In instances wherein at least one of the donor groups is —O—, the cyclic ligand is a "crown ether" type compound, with a typical example being wherein each D is oxygen and each L is —(CH$_2$)$_2$— and x is 2. Specific $\beta$-diketonate metal complexes which have been synthesized and have shown to be usefully volatile for CVD applications include 1,4,10,13-tetra-oxo-7,16-diazacyclooctadecane (4-13-diaza-18-crown-6), 1,4,7,10,13,16-hexathiacyclooctadecane (18-ane-S$_6$) and 1,4,7,10,13,16-hexaoxacyclooctadecane (18-crown-6).

The $\beta$-diketonate complexes of this invention cleanly and readily volatilize into the gas phase to yield a stable vapor at significantly lower temperatures than similar compounds without associated cyclic ligands. It has also been found, however, that when the associated cyclic ligand contains less than 6 donor groups, this improvement in volatility is not realized. The probable reason that ligands containing less than 6 donor groups such as 15-crown-5 do not show enhanced volatility is that $Ba^{+2}$ and $Sr^{+2}$ ions interact more strongly with 18-crown-6 than with 15-crown-5 (see R. M. Izatt, et al J. Am. Chem.Soc. 98, 7620 (1976)) and this is related to the "fit" of the metal ion into the macrocyclic cavity of the crown ligand. If the crown ligand is too small to accommodate the cation, a less stable complex results. With the donor atoms of the crown ligand being unable to achieve optimal interactions with the metal ions, more highly associated and larger molecular structures are likely to result. In some cases where the metal ion is too large, it may actually coordinate to two crown ligands (I. Bernal, Stereochemical and Stereophysical Behavior of Macromolecules vol. 2, 126–131, (1987)). This tendency away from monomeric structures evidently manifests itself in the observed lower volatility of the 15-crown-5 complexes.

Conversely, the use of crown ligands containing at least 6 donor groups is unlikely to result in more than one metal ion becoming coordinated within the macrocycle due to the resultant unfavorable build-up of electrostatic charge density. Therefore, single $Ba^{+2}$ or $Sr^{+2}$ ions should be readily accommodated within crown ligands of the same or larger size than those macrocyclic-type compounds which contain 6 or more donor atoms i.e. 18-crown-6. Thus, it is concluded that barium and strontium crown ligand compounds, of the type described in this disclosure wherein the crown ligand has the same or more donor groups than 18-crown-6, hold the potential to be more volatile than their parent non-crown ligand compounds due to effective metal ion encapsulation to yield monomeric volatile compounds.

EXPERIMENTAL

In the following examples, temperatures are set forth uncorrected in degrees celcius. Unless otherwise noted, all parts and percentages are by weight.

1,1,1,5,5,5-hexafluoro-2,4-pentanedione was purchased from Fairfield Chemical Company (P.O. Box 20, Blythewood, S.C. 29106). Barium hydride, strontium hydride and calcium hydride were obtained from Cercac Chemical Company (407 North 13th Street, Milwaukee, Wis. 53233). HPLC grade tetrahydrofuran (THF) was distilled from calcium hydride under nitrogen prior to use. All operations in the preparation of metal complexes were carried out using standard Schenk line techniques described by D. F. Shriver in the "Manipulation of Air Sensitive Compounds" McGraw-Hill Publishing Company.

$^1H$, $^{19}F$, and $^{13}C$ spectra were recorded using Bruker ACP-300 and SY-200 Nuclear Magnetic Resonance spectrometers.

Synthesis of Alkaline Earth β-Diketonate Complexes and Their Associated Volatile Crown Ligand Complexes The following represents a generic synthesis. Alkaline earth metal hydride (0.005 moles) and crown ether (0.005 moles) are charged into a 500 ml Schlenk flask fitted with a nitrogen inlet, magnetic stir bar and capped with a rubber septum. 50 ml of dry THF are added via canula then the β-diketone ligand (0.01 moles) is added dropwise via syringe over a 10 minute period with stirring. Hydrogen gas steadily evolves. When the last trace of hydride is digested, the reaction mixture is filtered to remove any turbidity, the solvent stripped off under vacuum and the resultant complex sublimed under dynamic vacuum ($10^{-3}$ torr) between 150° and 200°. The sublimation process is repeated until the sublimate is isolated as a pure white crystalline solid, typically three sublimations. This preparative procedure is also followed for the preparation of the parent β-diketonate complexes but the addition of crown ether is omitted. Analytical data for various alkaline earth β-diketone complexes synthesized in accordance with this procedure is reported in Table 1 below.

TABLE 1

| Complex | Yield | NMR (in deuteroacetone) | |
|---|---|---|---|
| $Ba^{+2}(hfac)_2$ | 41% | $^1H$ | δ5.7(S, 2H); |
| | | $^{19}F$ | δ77.1(S, 12F) |
| | | $^{13}C$ | δ86(S, 2C); δ119(Q, 4C); δ175(Q, 4C) |
| $Ba^{+2}(hfac)_2\cdot 18$-crown-6 | 82% | $^1H$ | δ3.8(S, 24H); δ5.65(S, 2H) |
| | | $^{19}F$ | δ−77.6(S, 12F) |
| | | $^{13}C$ | δ71.0(S, 12C); δ87.0(S, 2C); δ120.0(Q, 4C); δ175.0 (Q,4C) |
| $Ba^{+2}(hfac)_2\cdot 4,13$-diaza-18-crown-6 | 66% | $^1H$ | δ2.9(S, 8H); δ3.7(S, 16H); δ5.62(S, 2H) |
| | | $^{19}F$ | δ−77.6(S, 12F) |
| | | $^{13}C$ | δ48.9(S, 4C); δ70.9(S, 4C) δ71.7(S, 4C); δ86.0(S, 2C) δ119.2(Q, 4C); δ174.3(Q, 4C) |
| $Ba^{+2}(hfac)_2\cdot 15$-crown-5 | 22.5% | $^1H$ | δ3.85(S, 20H); δ5.7(S, 2H); δ(5.62(S, 2H) |
| | | $^{19}F$ | δ−76.8(S, 12F) |
| | | $^{13}C$ | δ69.0(S, 10C); δ87.0(S, 2C) δ119.0(Q, 4C); δ175.0(Q, 4C) |
| $Sr^{+2}(hfac)$ | 30.8 | $^1H$ | δ5.7(S, 2H) |
| | | $^{19}F$ | δ081.4(S, 12F) |
| | | $^{13}C$ | δ87(S, 2C); δ(120(Q, 4C); δ176(Q, 4C) |
| $Sr^{+2}(hfac)_2\cdot 18$-crown-6 | 69% | $^1H$ | δ3.7(S, 24H); δ5.7(S, 2H) |
| | | $^{19}F$ | δ−81.1 |
| | | $^{13}C$ | δ71(S, 12C); δ87(S, 2C); δ120(Q, 4C); δ175(Q, 4C) |
| $Sr^{+2}(hfac)_2\ 4,13$-diaza-18-crown-6 | 63.4% | $^1H$ | δ2.8(bs, 8H); δ3.7(S, 16H); δ5.75(S, 2H) |
| | | $^{19}F$ | δ−81.1 |
| | | $^{13}C$ | δ69(S, 12C); δ95.5(S, 2C); δ119(Q, 4C); δ175(Q, 4C) |
| $Sr^{+2}(hfac)_2\cdot 15$-crown-6 | 38.6% | $^1H$ | δ3.9(S, 20H); δ5.7(S, 2H) |
| | | $^{19}F$ | δ−77(S, 12F) |
| | | $^{13}C$ | δ69(S, 12C); δ95.5(S, 2C); δ119(Q, 4C); δ175(Q, 4C) |
| $Ca^{+2}(hfac)_2$ | 77% | $^1H$ | δ5.85(S, 2H) |
| | | $^{19}F$ | δ−81(S, 12F) |
| | | $^{13}C$ | δ89(S, 2C); δ119(Q, 4C); δ117(Q, 4C) |
| $Ca^{+2}(hfac)_2\cdot 18$-crown-6 | 58.8% | $^1H$ | δ3.8(bs, 24H); δ5.8(S, 2H) |
| | | $^{19}F$ | δ−76.8(S, 12F) |
| | | $^{13}C$ | δ65(bs, 12C); δ88(S, 2C); δ119(Q, 4C); δ176(Q, 4C) |
| $Ca(hfac)_2\cdot 4,13$-diaza-18-crown-6 | 63.0% | $^1H$ | δ2.84(M, 8H); δ3.70(S, 16H); δ5.75(S, 2H) |
| | | $^{19}F$ | δ−76.7 |
| | | $^{13}C$ | δ49(S, 4C); δ71(S, 4C); δ72(S, 4C); δ87(S, 2C); δ119(Q, 4C); δ175(Q, 4C) |
| $Ca^{+2}(hfac)_2\cdot 15$-crown-5 | 20% | $^1H$ | δ3.85(S, 2H); δ5.75(S, 20H) |
| | | $^{19}F$ | δ−81.4 |
| | | $^{13}C$ | δ69(S, 10C); δ88(S, 2C); δ119(Q, 4C); δ176(Q, 4C) |

EXAMPLE 1

Figure 2:
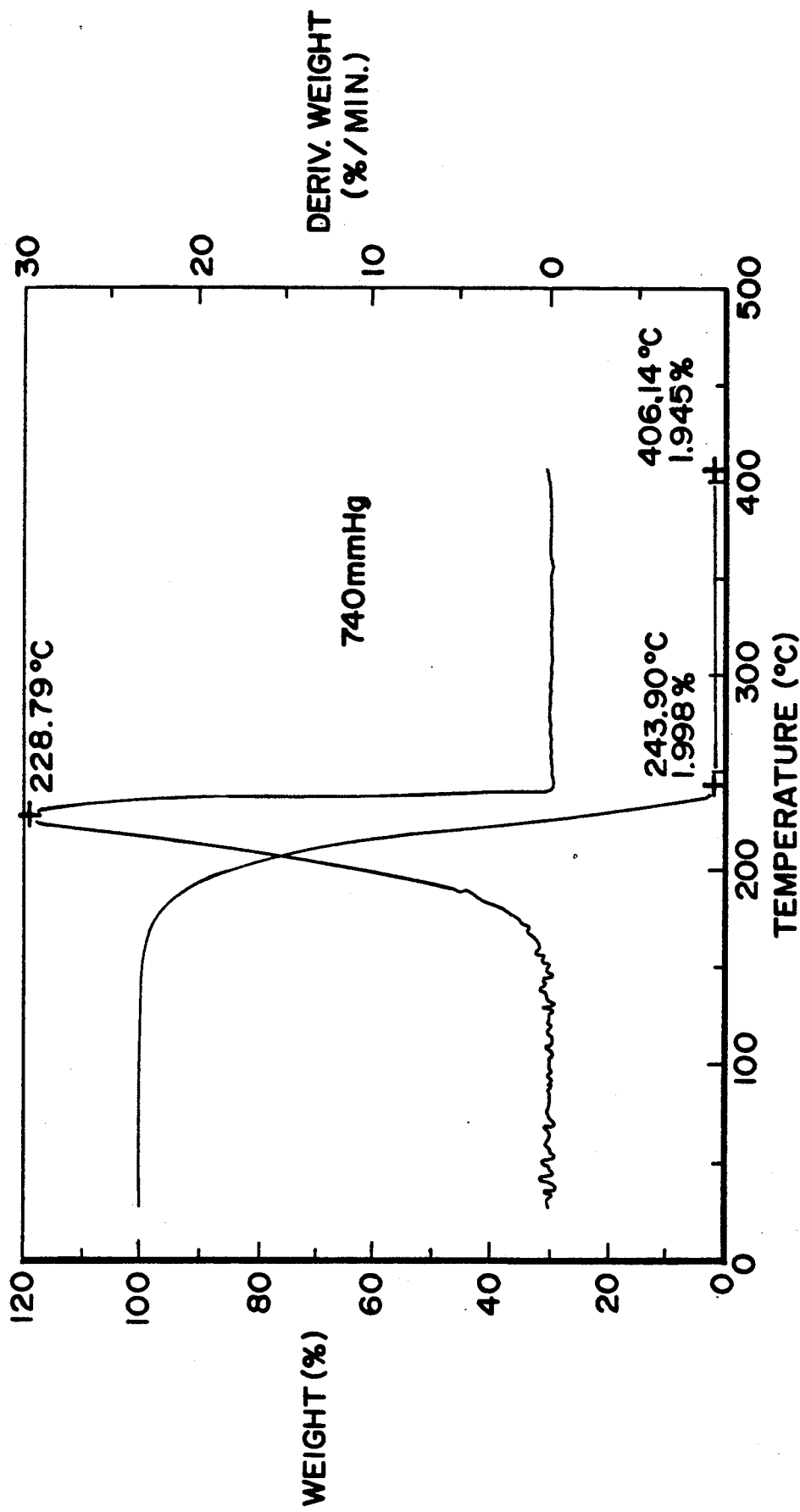
FIG. 2 is a graph of the sublimation characteristics of Ba(hfac)$_2$4,13-diaza-18-crown-6.
Figure 3:
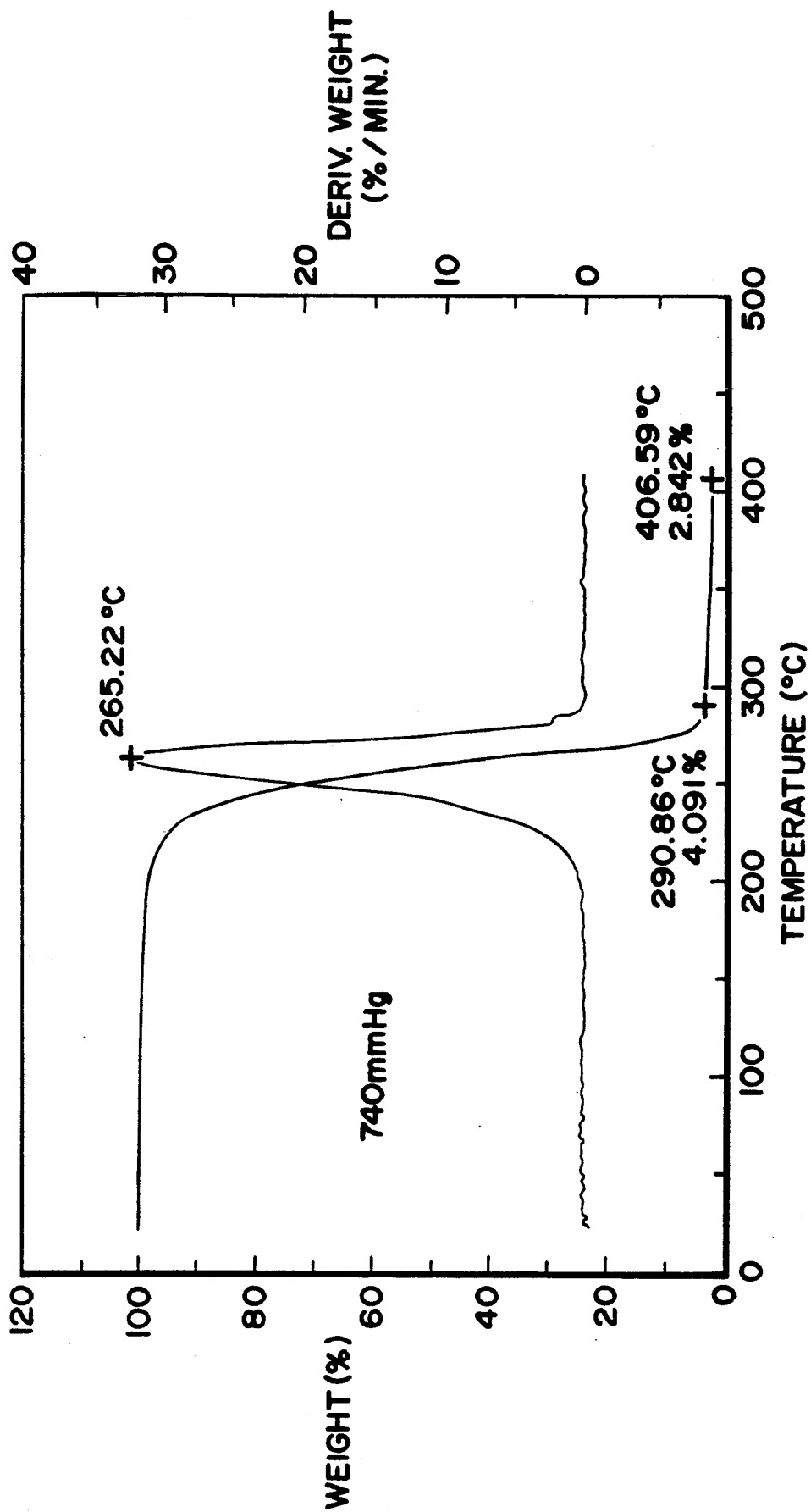
FIG. 3 is a graph of the sublimation characteristics of Ba(hfac)$_2$.
Figure 4:
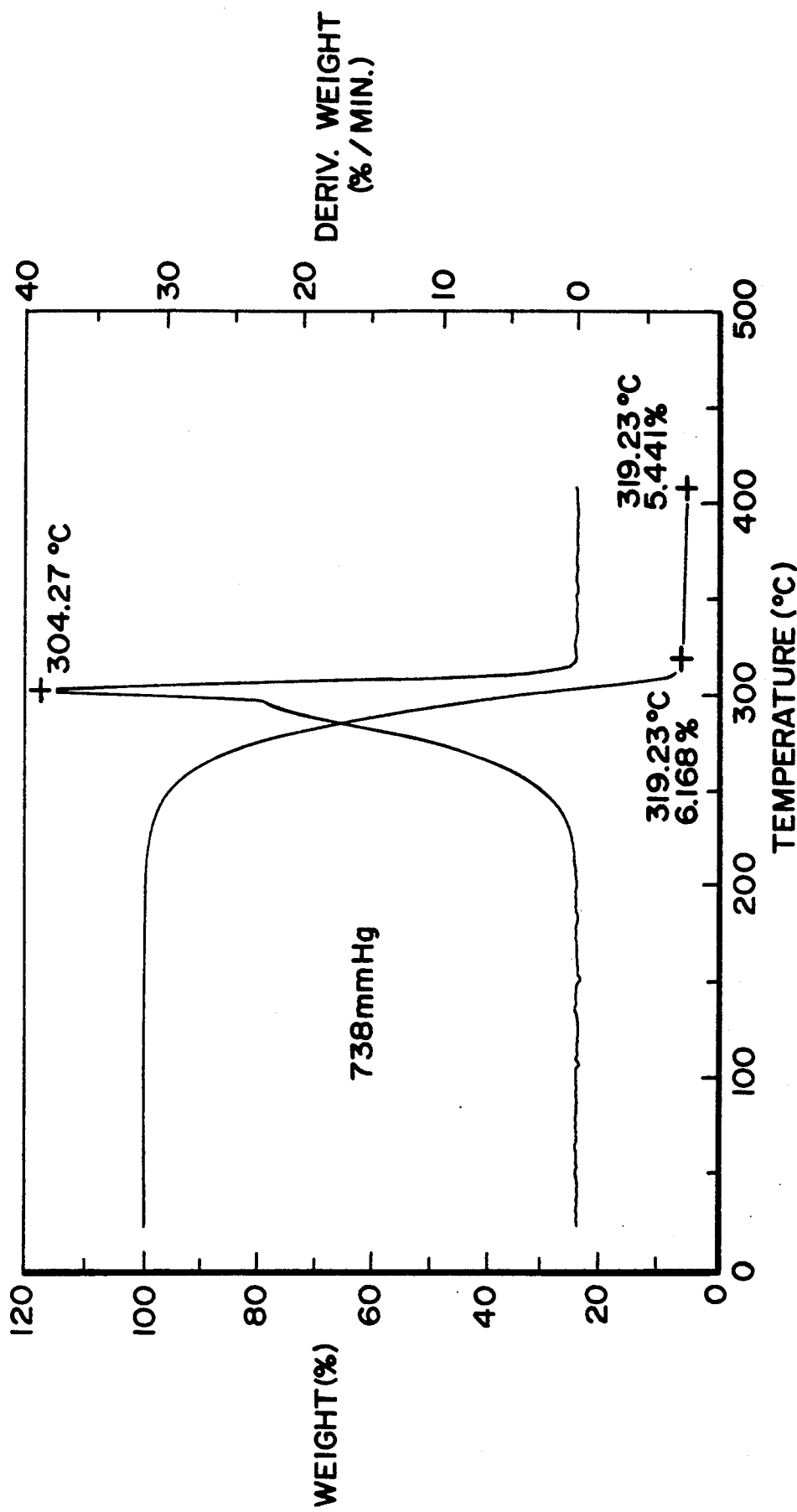
FIG. 4 is a graph of the sublimation characteristics of Ba(hfac)$_2$15-crown-5.

Experiments were carried out to demonstrate the sublimation characteristics of the metal complexes of the present invention. Volatility studies were carried out for barium(hfac)$_2$18-crown-6 and barium(hfac)$_2$4,13-diaza-18-crown-6. Volatility was determined by a thermogravimetric technique that consisted of measuring the weight loss of a sample of complex heated at 10°/min @ 20 torr pressure. For comparison, two barium β-diketonates, barium(hfac)$_2$ without an associated cyclic ligand and barium(hfac)$_2$15-crown-5 (only 5 donor groups) were also tested by the same procedure. The results of the tests are illustrated by the graphs of FIG. 1 for the complex containing 18-crown-6, and FIG. 2 for the complex containing 4,13-diaza-18-crown-6. The results for barium(hfac)$_2$ without the associated cyclic ligand is illustrated by the graph of FIG. 3 and barium(hfac)$_2$15-crown-5 by the graph of FIG. 4. Additionally, the results from the graphs are also presented in tabular form in Table 2 below.

TABLE 2

| FIG. | Column 1<br>Temperature at which the first derivative of weight loss shows a maximum | Column 2<br>Weight of residue remaining at 30° C. higher than temperature listed in column 1. |
| --- | --- | --- |
| 1 | 246 | 2.272% |
| 2 | 229 | 1.998% |
| 3 | 265 | 4.091% |
| 4 | 304 | 6.168% |

Inspection of Table 2 and FIGS. 1–4 clearly illustrate that the barium β-diketonate with no added crown ether (FIG. 3) and the barium(hfac)$_2$-15-crown-5 complex (FIG. 4) volatize at substantially higher temperatures and have a greater weight of residue than the samples with either 18-crown-6 or 4,13-diaza-18-crown 6.

EXAMPLE 2

Experiments were carried out in accordance with the procedures set out in Example 1 above to determine the sublimation characteristics of the corresponding strontium (hfac)$_2$ complexes. The results obtained from these experiments showed that strontium (hfac)$_2$ 18-crown 6 and strontium (hfac)$_2$ 4,13-diaza-18-crown-6 both sublime at relatively low temperatures, i.e. 216° and 190° C. respectively, with no significant chemical degradation. Conversely, the strontium (hfac)$_2$ without a crown ligand showed significant thermally induced degradation, and the strontium (hfac)$_2$ 15-crown-5 had an extremely high sublimation temperature, i.e. about 273° C.

EXAMPLE 3

Experiments were carried out in accordance with the procedures set out in Example 1 above to determine the sublimation characteristics of the corresponding calcium (hfac)$_2$ complexes. The results obtained from these experiments showed that both calcium (hfac)$_2$ 18-crown-6 and calcium (hfac)$_2$ 4,13-diaza-18-crown-6 sublime at relatively low temperatures, i.e. about 197° and 188° C. respectively, with no significant chemical degradation. Conversely, the calcium (hfac)$_2$ without a crown ligand showed a higher degree of degradation and a higher sublimation temperature, i.e. about 219° C. The calcium (hfac)$_2$ 15-crown-5 also exhibited chemical degradation as well as an extremely high sublimation temperature, i.e. about 295° C.

The results of the above examples clearly show that the complexes of the present invention exhibit characteristics which make them useful in CVD operations. The examples also demonstrate the criticality of the crown ligand; and also the need for at least 6 donor groups in the crown.

Having thus described the present invention, what is now deemed appropriate for Letters Patent is set out in the following appended claims.

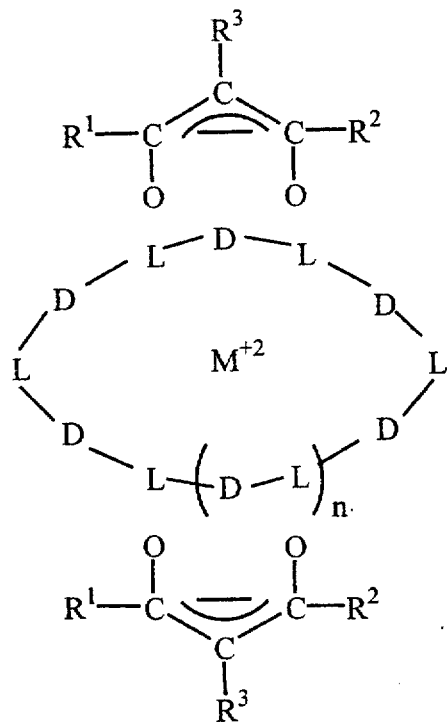

What is claimed is:

1. A volatile, divalent metal β-diketonate complex represented by the structural formula:

wherein:
$M^{+2}$ is a divalent metal ion from the alkaline earth series;
each $R^1$ and $R^2$ are independently a linear or branched $C_1$-$C_4$ perfluoroalkyl group or a fluorophenyl group;
each $R^3$ is independently H, a halogen, phenyl or a $C_1$-$C_4$ alkyl or fluoroalkyl group;
each D is independently a donor group selected from $$-O-, -S-, -\underset{R}{N}-, \text{ or } -N=\underset{R}{C}-$$

wherein R is H or $C_1$-$C_4$ alkyl;
L is $(CR_2)_x$ wherein each R is independently H or $C_1$-$C_4$ alkyl and x is an integer from 1 to 4, or L is part of a cyclic aromatic or aliphatic ring; and
n is an integer from 1 to 3.

2. The compound in accordance with claim 1 wherein $M^{+2}$ is selected from the group consisting of: $Ca^{+2}$, $Sr^{+2}$, and $Ba^{+2}$.

3. The compound in accordance with claim 2 wherein each D is —O—.

4. The compound in accordance with claim 3 wherein each L is —(CH$_2$)$_2$—.

5. The compound in accordance with claim 4 wherein n is 1.

6. The compound in accordance with claim 1 wherein D and L together form 1,4,10,13-tetra-oxo-7,16-diazacyclooctadecane.

7. The compound in accordance with claim I wherein D and L together form 1,4,7,10,13,16-hexathiacyclooctadecane.

8. The compound in accordance with claim 1 wherein D and L together form 1,4,7,10,13,16-hexaoxacyclooctadecane.

9. The compound in accordance with claim 8 wherein $M^{+2}$ is $Ba^{+2}$.

10. The compound in accordance with claim 9 wherein each $R^1$ and $R^2$ are $CF_3$ and each $R^3$ is H.

11. The compound in accordance with claim 1 wherein L is

* * * * *

UNITED STATES PATENT AND TRADEMARK OFFICE
CERTIFICATE OF CORRECTION

Page 1 of 2

PATENT NO. : 5,252,733

DATED : October 12, 1993

INVENTOR(S) : John A. T. Norman and Guido P. Pez

It is certified that error appears in the above-identified patent and that said Letters Patent is hereby corrected as shown below:

Column 3, lines 40-58 and col. 8, lines 1-19, the structure formula is incorrect. There should be a resonating bond in each of the two diketone ligands and an $M^{+2}$ moiety in the ring, as per attached page.

Signed and Sealed this

Seventh Day of March, 2000

Attest:

Q. TODD DICKINSON

Attesting Officer

Commissioner of Patents and Trademarks

UNITED STATES PATENT AND TRADEMARK OFFICE
CERTIFICATE OF CORRECTION

PATENT NO. : 5,252,733
DATED : October 12, 1993
INVENTOR(S) : John A. T. Norman and Guido P. Pez It is certified that error appears in the above-indentified patent and that said Letters Patent is hereby corrected as shown below: